United States Patent [19]

Link et al.

[11] 4,324,932
[45] Apr. 13, 1982

[54] PROCESS FOR THE MANUFACTURE OF VINYL CHLORIDE BY THE THERMAL CRACKING OF 1,2-DICHLOROETHANE

[76] Inventors: Gerhard Link, Jakob-Steffanstr. 14, 65 00 Mainz; Josef Riedl, Kantstr. 53, 8261 Burgkirchen; Walter Fröhlich, Kampenwandstr. 11, 8261 Burgkirchen; Reinhard Krumböck, Lohnerstr. 40, 8261 Burgkirchen, all of Fed. Rep. of Germany

[21] Appl. No.: 169,789

[22] Filed: Jul. 17, 1980

[51] Int. Cl.³ .............................................. C07C 21/06
[52] U.S. Cl. .................................................... 570/226
[58] Field of Search ......................................... 570/226

[56] References Cited

U.S. PATENT DOCUMENTS 2,762,850 9/1956 Lenz ................................. 570/226 X
3,689,579 9/1972 Baader et al. ....................... 570/226
3,732,322 5/1973 Kawaguchi et al. ................ 570/226
3,920,761 11/1975 Krome ................................ 570/226

FOREIGN PATENT DOCUMENTS 683876 4/1964 Canada ................................. 570/226

Primary Examiner—John Doll
Attorney, Agent, or Firm—Wilson, Fraser, Barker & Clemens

[57] ABSTRACT

The description covers a process for the manufacture of vinyl chloride by thermal cracking of 1,2-dichloroethane. The hot gas leaving the reaction furnace is cooled to the inlet temperature of the column in which the hydrogen chloride is separated from the products of thermal cracking of the 1,2-dichloroethane. Within the range of 560° to 480° C. and of 220° to 120° C., one or more cooling stages are applied through which the reaction gas mixture passes at high flow velocity, the cooling device being preferably a single-tube cooler. Starting from about 220° C., a liquid substantially consisting of 1,2-dichloroethane may be added intermittently. The heat transferred to the coolant in the stages of indirect cooling is preferably reused within the vinyl chloride manufacturing process.

10 Claims, 3 Drawing Figures

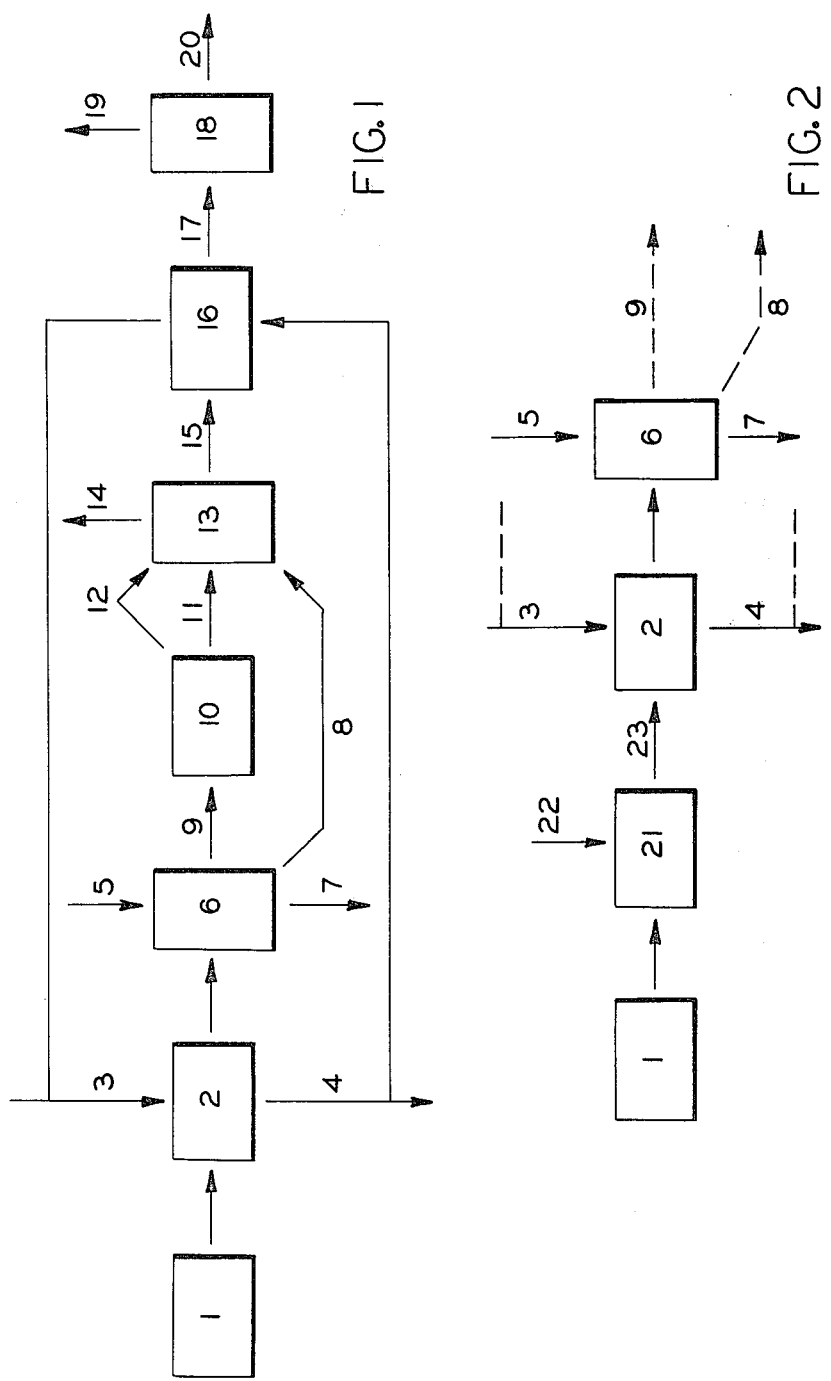

PROCESS FOR THE MANUFACTURE OF VINYL CHLORIDE BY THE THERMAL CRACKING OF 1,2-DICHLOROETHANE

BACKGROUND OF THE INVENTION

The present invention relates to a process for the manufacture of vinyl chloride and hydrogen chloride from 1,2-dichloroethane by thermal cracking of the 1,2-dichloroethane and subsequent cooling and rectification of the product mixture.

The thermal cracking of 1,2-dichloroethane is performed according to known processes in which the 1,2-dichloroethane is subjected to indirect heating in a reaction furnace and split into vinyl chloride and hydrogen chloride at temperatures ranging from 480° to 560° C. Thermal cracking is not complete, but yields a product mixture which contains numerous by-products of different chemical composition apart from 1,2-dichloroethane and the main products referenced above. Among said by-products, saturated and unsaturated aliphatic compounds, aromatics and carbon black may be cited. Deposits of carbon black and coke in the reaction furnace require a shutdown of the furnace at intervals of some months for decoking operations. The formation of by-products is partly attributable to the fact that attempts to produce absolutely pure dichloroethane at economically justified costs, have so far been unsuccessful. Another cause is that the reaction products are thermally unstable at the required high temperature and undergo decomposition to carbon in a series of further reactions.

As described in patents on this subject, the temperature of the hot reaction gases can subsequently be lowered indirectly with the aid of a cooling fluid and directly with the aid of precooled reaction product.

In practice, however, the method of indirect cooling has proved not to be advantageous because undesirable and troublesome coke deposits were encountered within a short time.

In a cooling system of conventional design for lowering the temperature of the hot reaction gases from 540° C. to 200° C., an undesirable pressure drop will be encountered after a few weeks of service time owing to increasing coke deposits in the tubes.

Therefore, continued efforts have been made to end as quickly as possible the thermal instability of the hot gas mixture leaving the reaction furnace. This has been achieved through direct cooling by continuous injection of cold liquid dichloroethane into the hot gas stream. By this method, the reaction gases were quenched to a temperature at approximately 130° to 60° C. Within this temperature range, secondary reactions causing coke deposits are generally no longer encountered. This cooling causes partial condensation of the reaction gases. Carbon black particles entrained by the gas stream from the reaction furnace are suspended in the cooled liquid product and can be retained by filtration. For the further processing of the reaction product mixture, the individual components, i.e. hydrogen chloride, vinyl chloride and unconverted 1,2-dichloroethane are isolated in the sequence of their boiling points from the higher-boiling substances, and the 1,2-dichloroethane is recycled to the reaction furnace.

According to a publication which appeared in "Hydrocarbon Processing", November, 1975, pages 214/215 the commercial processes of the two principal licensors make use of the direct cooling of the hot reaction gases by means of cooled liquid product in a multitude of industrial plants.

The disadvantage of the method of direct cooling which has been practiced for more than 20 years is the high energy demand for pumping the recycle flow of reaction product and the complete loss of the heat supplied to the reaction furnace.

It is also known to separate carbon black from the effluent reaction gases by means of a cyclone with subsequent cooling by air; however, as compared to cooling with liquid 1,2-dichloroethane, this method requires equipment of considerably greater volume for high throughput rates without eliminating the undesirable heat losses.

The description also covers the cooling of the reaction gases with water in one stage. In view of the low temperature level to which the gases must be cooled to undergo partial condensation before being fed to the first column for separating the hydrogen chloride, this method is largely inadequate to utilize the heat content of the reaction gases. Moreover, the description contains no information on the actual cooling rate of the reaction gases nor on the service time of the coolers.

Another disadvantage of direct cooling is the volume of equipment and machinery required. For lowering the temperature of the hot reaction gases from approximately 530° C. to approximately 80° C., for example, the quantity of recycle fluid is about 17 times the quantity of liquid product. The heat absorbed by the recycle fluid is dissipated on the reaction product side for the temperature range from about 80° C. to 40° C. and on the cooling water side at a temperature of about 25° to 35° C. Cooling of the liquid recycle fluid must be maintained and secured at any rate to avoid a dangerous temperature rise in the quench tower. The safety system provided for this purpose comprises a temperature interlock for the reaction furnace actuated by a temperature sensing element at the quench tower outlet, and of an emergency power set and a steam turbine for driving at least one fluid recycle pump. At the time of shutting down the plant, this is the only possibility to dissipate without risk, through vaporizing 1,2-dichloroethane, the heat stored in the furnace bricklining.

The reaction furnace is generally placed in the immediate vicinity of the quench tower. The connecting line, for example, has a length of only 1 to 2 m. The admission of reaction gas into a quench tower at a temperature of 530° C. is bound to cause excessive stresses in the material unless injection of cold liquid recycle product from the top is safeguarded. Under extreme conditions explosive fluid may escape through leaks in the quench tower in the immediate vicinity of the furnace burners.

SUMMARY OF THE INVENTION

The present invention is intended to eliminate the disadvantages of the processes described.

According to the invention, the problem is solved by a process for the manufacture of vinyl chloride by thermal cracking of 1,2-dichloroethane in which the reaction gas mixture leaving the reaction furnace is cooled in more than one stage by means of a liquid or gaseous coolant with subsequent fractionating distillation, the process incorporating the improvement which comprises the reaction gas mixture being cooled per second by an average rate of at least 1/10 of the temperature of the reaction gas mixture entering the indirect stage until a temperature ranging from 220° C. to 120° C. is reached, the heat transferred to the coolant being utilized for heating any process equipment and the reaction gas mixture together with the resulting condensate, if any, being further cooled directly or indirectly in at least one subsequent stage.

The term "coolant" is intended to mean a substance or a mixture of substances which serves for the absorption and dissipation of heat and which can conveniently be transferred from the point of heat absorption to the area of heat dissipation.

Indirect cooling is preferably performed by means of a heat exchanger in which the reaction gas to be cooled passes through a single tube that is surrounded by the coolant. This method avoids the formation of areas or vortex pockets in the product stream where the cooling rate would be lower than required. Heat exchangers of different design, such as plate heat exchangers or tubular heat exchangers in which the coolant passes through the tubes while the reaction gas is admitted to the shell side and vice versa are also adequate.

The direct cooling of the reaction gas can preferably be performed by contacting the gas with a cold liquid containing at least 50% by weight of 1,2-dichloroethane. This is realized, for example, by injecting the liquid into the gas stream or by admitting a counter-current flow of liquid in a column. Purified recycle 1,2-dichloroethane is preferably used for this purpose.

For the indirect cooling of the hot reaction gases to 220°–120° C., the average cooling rate per second shall be at least 1/10 of the temperature (in the following referred to as TA, in terms of degrees centigrade) of the reaction gases entering the indirect cooling stage. The rate is determined by reading the temperature difference between the reaction gas the inlet of the cooling stage and the gas at the outlet with due consideration to the average residence time of the reaction gas during cooling. At cooling rates below TA/10 s, side reactions are bound to occur and cause excessive pollution of the reaction gas mixture with by-products. The upper limit of the cooling rate is set by restrictions of mechanical design of the cooler and by economic considerations. In general, the average cooling rates per second do not exceed $\frac{1}{2}$ of the inlet temperature TA. The average cooling rate per second of the reaction gas mixture is maintained at $\frac{1}{4}$ to 1/9 of the inlet temperature TA of the reaction gas mixture and particularly at 1/5 to 1/7 of the inlet temperature TA.

Referring to the conventional thermal cracking of 1,2-dichloroethane, the reaction gas mixture leaves the furnace at a pressure of 1.5 to 2.5 MPa and a temperature of 560° to 480° C. Then according to the instant invention it is cooled indirectly by means of a liquid or gaseous coolant to a temperature of 220° to 120° C., preferably of 200° to 150° C. Cooling to a temperature level above 220° C. is possible but less advisable economically because of its adverse effect on heat utilization. If the gas is cooled to less than 120° C., the temperature of the coolant is no longer sufficiently raised to ensure a good and versatile utilization of the heat.

Preference is given to a coolant that is liquid at 100° C. and whose vapour pressure does not exceed 2.5 MPa at 220° C. Such coolants are, for example, sparingly volatile mineral oils, diphenyl, silicone oils.

Another preferred version of the present process proceeds with indirect cooling by means of a coolant whose boiling point is between 70° to 110° C. at a pressure of 98.1 kPa, for example water, 1,2-dichloroethane or liquid mixtures which contain a minimum of 50% by weight of 1,2-dichloroethane.

The balance of the mixture can consist of substances which preferably do not attack the material of the heat exchanger. If chlorine or hydrogen-chloride-bearing 1,2-dichloroethane is used, the material of construction of the heat exchanger must be selected accordingly.

In another preferred version of the process according to this invention, the reaction gas mixture leaving the reaction furnace at a temperature of about 560° to 480° C. is first cooled directly by contacting it with a liquid product which contains a minimum of 50% by weight of 1,2-dichloroethane and then indirectly by means of a liquid or gaseous coolant, said indirect cooling being initiated only when the reaction gas mixture has reached a temperature of about 430° to 350° C., preferably about 400° to 370° C. and being continued until a temperature of 220° to 120° C., preferably of 200° to 150° C. has been reached, the heat absorbed by the coolant being utilized for heating any process equipment and the reaction gas mixture together with any resultant condensate being further cooled directly or indirectly in at least one subsequent stage.

Contacting is preferably performed by injection or any other method of fine distribution, such as spreading to a fine film, of the product containing the liquid 1,2-dichloroethane in a space confining the flow of the hot reaction gas mixture.

The liquid 1,2-dichloroethane may contain up to 50% by weight of other substances which undergo no or little chemical reaction with the hot reaction gas mixture. Preference is given to using a 1,2-dichloroethane produced by direct chlorination and/or by oxychlorination of ethylene and/or obtained from the thermal cracking process for producing vinyl chloride by cooling the reaction gases and which contains the by-products commonly known for these processes.

For the indirect cooling to 220°–120° C. the same average cooling rates are used as cited before. At relatively low inlet temperatures TA of the reaction gas mixture entering the indirect cooling stage it is generally possible to apply slightly increased average cooling rates as compared to the preferred range of TA/4 to TA/9 referenced above. At TA=360° C., for example, good results are obtained at cooling rates of 100° to 120° C./s=TA/3.2 s to TA/2.66 s without an excessive volume of process equipment.

For the version of the process according to this invention incorporating the precooling of the hot reaction gas mixture by means of 1,2-dichloroethane, the subsequent indirect cooling is preferably performed with the same coolants that are used for the process without precooling with 1,2-dichloroethane.

In another preferred version of the process, the reaction gas mixture is cooled in the following stages:

In a first stage, the temperature is lowered by indirect cooling from the reaction furnace outlet temperature to about 220° C.; it is further lowered to about 140° C. in a second stage by partly direct, partly indirect cooling with a liquid consisting substantially of 1,2-dichloroethane, and is subsequently lowered in at least one further stage by direct or indirect cooling to the inlet temperature of the column in which the hydrogen chloride is separated from the products of thermal cracking of 1,2-dichloroethane.

As outlined for the other versions of the process according to this invention, cooling in the first and second stage is preferably performed in a heat exchanger in which the reaction gas to be cooled passes through a single tube which is surrounded by the coolant. Heat exchangers of different design may also be used, for example plate heat exchangers or tubular heat exchangers in which the coolant passes through the tubes or plates while the reaction gas is admitted to the shell side and vice versa. Both the single-tube heat exchangers and the other designs may feature a continuous or intermittent reduction of their cross-sectional area to compensate in whole or in part the reduction of the gas volume caused by cooling and, consequently, to maintain a more-uniform flow velocity than would be possible with a constant cross-sectional area.

The average cooling rate of the reaction gas in the first stage shall be at least 1/10 per second and in the second stage at least 1/5 per second of the temperature at which the reaction gas enters into the respective cooling stage. The average cooling rate is determined by instrument readings as outlined before. The upper limit of the cooling rate is set by restrictions of mechanical design of the cooler and by economic considerations. In general, the average cooling rates per second do not exceed $\frac{1}{2}$ of the inlet temperature in the first stage of 1/1 in the second stage. The average cooling rate of the reaction gas mixture is preferably maintained at $\frac{1}{4}$ to 1/9 per second in the first cooling stage and $\frac{1}{2}$ to $\frac{1}{4}$ per second of the inlet temperature TA in the second stage. Referring particularly to the first stage, a cooling rate of 1/5 to 1/7 of the inlet temperature of this stage is applied.

In the first stage, the temperature of the reaction gas mixture is lowered from the reaction furnace outlet temperature, in general about 560° to 480° C., to a temperature of 250° to about 170° C., preferably to about 220° C., while the reaction gas mixture is further cooled in the second stage from the outlet temperature of the first stage to about 150° to 110° C., preferably to about 140° C.

Between the two cooling steps which are preferably performed in two separate items of equipment but which can also be realized in a common single-cooler, provision is made for an injection device for a liquid which consists substantially of 1,2-dichloroethane. This injection device may be a single tube which is preferably provided with an injection liquid distributor at the end reaching into the reaction-gas-carrying tube, for example a nozzle or perforated plate or sphere.

The injection line for the liquid containing 1,2-dichloroethane is preferably equipped with a conveying device outside the reaction gas cooler, for example a pump, which permits feeding against the prevailing back-pressure relatively large quantities of the liquid within a short time to the second-stage heat exchanger area containing the reaction gas mixture. In addition, it is advisable to equip the reaction gas line between the first and second cooling stage with a device, for example a pressure-regulated valve, which maintains a substantially constant pressure in the first cooling stage at the time of a sudden pressure drop in the second cooling stage.

During operation of the first and second cooling stages, a liquid substantially consisting of 1,2-dichloroethane is injected at intervals of 20 to 500 hours, preferably at intervals of 50 to about 200 hours, into the compartment containing the reaction gas mixture between the two cooling stages. The quantity of liquid injected is 1.5 to 5.0 kg/min. per kg/min. of reaction gas mixture passing through the cooling stages.

The intermittent injection of the liquid consisting substantially of 1,2-dichloroethane, contributes to extending the service time of the entire cooling system and to improving the heat transfer in the second cooling stage because this method prevents or at least substantially reduces the formation of deposits on the walls of the compartment containing the reaction gas in the second cooling stage, said formation of deposits being attributable to products originating from the reaction gas. If the liquid is injected at intervals exceeding substantially a period of 500 hours and for a time of less than one minute, the desired effect is not achieved or remains incomplete. The same applies if the quantity of injected liquid remains less than 1.5 kg/min. per kg/min. of reaction gas. If injection is performed at intervals of 120 hours and/or during a period of more than 30 minutes for each injection operation or if the quantity injected exceeds substantially 5.0 kg/min. per kg/min. of reaction gas, the heat transfer from the reaction gas mixture to the coolant in the second cooling stage is still satisfactory, but the quantity of heat transferred to the coolant becomes relatively small and the process less economical on the one hand and cumbersome and expensive on the other hand due to the frequent and/or abnormally large quantity of liquid injected. The quantity of reaction gas in kg/min. which passes through the cooling stages is easy to determine because it is practically equal to the quantity of 1,2-dichloroethane admitted to the reaction furnace.

The liquid substantially consisting of 1,2-dichloroethane may be pure, 1,2-dichloroethane or a mixture of dichloroethane with a portion of max. 50% by weight of other substances, referred to the liquid, particularly such substances which are obtained as normal impurities when producing 1,2-dichloroethane by the chorination of oxochlorination of ethylene or which, after thermal cracking, remain in the unconverted 1,2-dichloroethane after separation of the hydrogen chloride and the vinyl chloride; for example:

vinyl chloride; ethyl chloride; 1,1-dichloroethylene; 2-chlorine butadiene-(1,3); 1,1-dichloroethane; carbon tetrachloride; 1,1,2-trichloroethylene; 1,1, 2-trichloroethane; ethylene chlorohydrin; chloroform; benzene and other substances.

Preference is given to a liquid containing at least 60% by weight of 1,2-dichloroethane.

Results are particularly satisfactory if the liquid substantially containing 1,2-dichloroethane is injected into the reaction gas stream at a rate of 2.5 to 3.5 kg/min. per kg/min. of reaction gas ahead of the second cooling stage at the time and intervals outlined before.

The liquid substantially consisting of 1,2-dichloroethane is preferably injected into the reaction gas mixture at a temperature of 20° to 70° C. It is especially advisable to use a 1,2-dichloroethane obtained from the direct cooling (quenching) of the reaction gas ahead of a third cooling stage in which the temperature of the reaction gas is lowered to the inlet temperature of the column in which hydrogen chloride is separated from the products of thermal cracking of 1,2-dichloroethane, that means to a temperature of about 0° to 70° C.

The reaction gas leaving the second cooling stage at a temperature of 150° to 110° C. generally contains a certain portion of condensate, especially when a liquid substantially consisting of 1,2-dichloroethane is injected into the reaction gas mixture before or during the cooling of the reaction gas mixture in the second cooling stage at the rates defined above. This mixture of liquid and gaseous components is then cooled either directly by injecting further 1,2-dichloroethane or indirectly, for example by cooling with water or with liquid 1,2-dichloroethane, to the inlet temperature of the column in which the gaseous hydrogen chloride is separated, this cooling being preferably performed in another two stages. Before admission to this column, or ahead of the column between the second and third cooling stage, solid components are retained from the gas/liquid mixture by conventional methods, for example filtration, and separated from downstream processing steps. The further processing of the cooled 1,2-dichloroethane-containing reaction gas mixture for separating the hydrogen chloride, the vinyl chloride and further compounds having a lower or higher boiling point than 1,2-dichloroethane is realized by known methods generally by distillation, a certain quantity of chlorine being added if necessary. The recovered and purified 1,2-dichloroethane is recycled to the process as usual, that means it is subjected again to thermal cracking; as described before, part of it may be used to make-up liquid for reaction gas cooling.

The heat absorbed by the coolant during the single-stage or multi-stage indirect cooling step to reaction gas outlet temperatures of 220° to 120° C. may be utilized for heating various items of process equipment, for example of equipment provided for heating and vaporizing the 1,2-dichloroethane before the gas enters the reaction furnace or for heating liquid products which are admitted to the distillation equipment in the course of further splitting the condensed reaction gas mixture by distillation. The heat absorbed by the coolant during indirect cooling may also be utilized outside the process for producing vinyl chloride by thermal cracking of 1,2-dichloroethane, for example for the generation of electric power, for heating reaction vessels, rectification columns, or for the heating of buildings.

The heat exchangers used for the indirect cooling of the reaction gas mixture are preferably equipped with devices which indicate any leaks in the partition wall between reaction gas mixture and coolant so that effective action may immediately be taken to avoid serious operating disturbances. It is advisable to provide for a second heat exchanger that can be taken in operation upon occurrence of any leaks or at the time when the service heat exchanger must be cleaned.

The process according to this invention avoids an essential portion of the equipment and machinery required for the direct cooling with the large quantity of recycle coolant. The quantity of coolant available in the heat exchanger for indirect cooling ensures a reliable dissipation of the heat absorbed by the reaction furnace in the event of a power failure in the plant.

In addition, the process according to the invention permits utilizing valuable thermal energy that has so far been lost, with consequent marked improvement of the economy of the process for the manufacture of vinyl chloride by the thermal cracking of 1,2-dichloroethane. Moreover, the dissipation of excess heat to cooling water and, consequently, environmental pollution, is markedly reduced.

BRIEF DESCRIPTION OF THE DRAWINGS

The schematic drawings, FIGS. 1, 2 and 3 show the route of the process according to the invention which is further explained by the examples 1 to 5. The feasibility of the process is not restricted to the examples described. Pressure ratings cited in the examples are given in terms of absolute pressure. For comparison, two tests (A and B) realized at low average cooling rates are incorporated.

DESCRIPTION OF PREFERRED EMBODIMENTS

Figure 3:
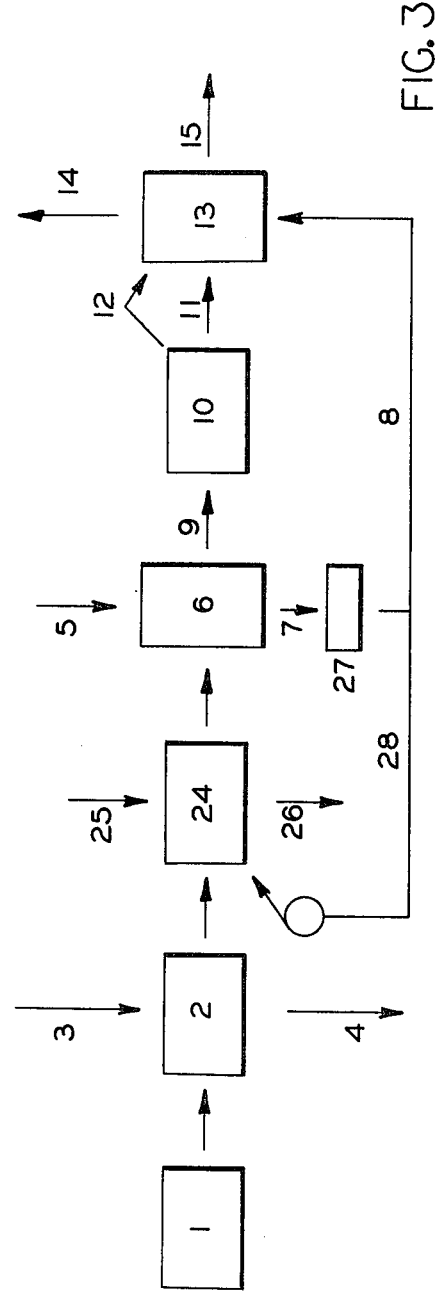

Referring to the flowsheet FIG. 1, the gas leaving reaction furnace 1 at a temperature of 480° to 560° C. is cooled in a heat exchanger 2 at a high flow velocity to a temperature level of 120° to 220° C., with partial condensation of the reaction gas at a pressure of 1.4 to 2.4 MPa. The energy of the reaction gas is transferred to a coolant, for example deionized water, which is admitted to heat exchanger 2 through line 3. The energy recovered from the reaction gas is carried off by the coolant through line 4 and can be utilized for heating purposes, for example for heating equipment which serves for splitting the reaction gas into its components, particularly for heating the product from which vinyl chloride is separated in a column. For further lowering the temperature of the reaction gas to 100° to 60° C., the gas is scrubbed in a device 6 with 1,2-dichloroethane of about 10° to 50° C., small black carbon particles entrained from the reaction furnace being simultaneously separated from the gas stream and discharged through line 7. Gaseous and liquid reaction products are withdrawn separately from scrubbing device 6. The liquid portion substantially consisting of 1,2-dichloroethane is admitted directly through line 8 to column 13 which serves for separating the hydrogen chloride. The gaseous portion is sent through line 9 to a device 10 in which it is cooled to 0° to 40° C. Both the liquefied portion and the residual gaseous portion are also sent through lines 11 and 12 to column 13. In this column, the hydrogen chloride is separated and discharged through line 14. The liquid bottom product is admitted through line 15 to a heat exchanger 16 which is preferably heated by the hot coolant from line 4. The cooled fluid is preferably returned to line 3. The hot bottom product from column 13 passes through line 17 into column 18 where vinyl chloride is separated and subsequently withdrawn through line 19. The liquid bottom product from column 18 is admitted by known methods through line 20 to at least one column where the product mixture is split further, particularly for recovering the 1,2-dichloroethane. The latter is returned to reaction furnace 1 after preheating, if any, by means of the hot coolant from line 4.

FIG. 2 shows a preferred version of the process according to this invention.

The gas leaving reaction furnace 1 at a temperature of 560° to 480° C. is admitted to a device 21 in which it is cooled to 430° to 350° C. by admitting, through line 22, controlled quantities of a liquid which contains not less than 50% by weight of 1,2-dichloroethane and which is at a temperature of about 10° to 50° C. The cooled gas and the vaporized portion of the liquid admitted are then sent through line 23 to heat exchanger 2 shown in FIG. 1 and further processed as shown in FIG. 1.

FIG. 3 shows another preferred version of the process according to this invention.

The gas leaving reaction furnace 1 at a temperature of 480° to 560° C. is cooled in a heat exchanger 2 at a high flow velocity to a temperature of about 221° C. and subsequently admitted to a second heat exchanger 24 where the temperature is further lowered to about 140°

C., with partial condensation of the reaction gas at a pressure of 1.4 to 2.4 MPa. The energy of the reaction gas is transferred to a coolant, for example deionized water which is admitted through lines 3 and 25 to heat exchangers 2 and 24. The energy recovered from the reaction gas is carried off by the coolant through line 4 and 26 and may be utilized for heating purposes, for example for heating process equipment which serves for splitting the reaction gas into its components, particularly for heating the product from which vinyl chloride is separated in a column or for heating the product from which 1,2-dichloroethane is separated in a column. For further lowering the temperature to a level of 70° to 60° C., the gas is scrubbed with 1,2-dichloroethane of about 10° to 50° C. admitted through line 5 to a device 6 where small carbon black particles entrained from the reaction furnace are simultaneously separated from the gas stream, withdrawn through line 7 and separated from the liquid in device 27. The purified liquid portions consisting substantially of 1,2-dichloroethane are partly admitted through line 8 to column 13 for separating the hydrogen chloride, partly fed at certain intervals through line 28 by means of a pump and a metering device into the second heat exchanger 24. The gaseous portions from device 6 are admitted through line 9 to a device 10 in which they are cooled to a level of 0° to 40° C. Both the liquefied portions and the residual gaseous portions are also sent through lines 11 and 12 to column 13. In this column, the hydrogen chloride is separated and subsequently discharged through line 14. The liquid bottom product is admitted through line 15 to further devices which serve for separating the vinyl chloride and for recovering unconverted 1,2-dichloroethane of optimum purity. The latter is returned to reaction furnace 1 after preheating, if any, by means of the hot coolant from line 4 (not shown).

EXAMPLE 1

Reference is made to flowsheet FIG. 1. The reaction furnace is fed hourly with 9.98 parts by weight of 1,2-dichloroethane having the following composition:

|  | wt. % |
|---|---|
| vinyl chloride | 0.1 |
| ethyl chloride | 0.004 |
| 1,1-dichloroethylene | 0.014 |
| 2-chlorobutadiene-(1,3) | 0.034 |
| 1,1-dichloroethane | 0.052 |
| carbon tetrachloride | 0.004 |
| benzene | 0.159 |
| chloroform | 0.011 |
| 1,1,2-trichloroethylene | 0.044 |
| 1,2-dichloroethane | 99.517 |
| 1,1,2-trichloroethane | 0.004 |
| ethylene chlorohydrin | 0.002 |
| unknown | 0.053 |

At a pressure of 2.1 MPa, 5.46 parts by weight per hour of 1,2-dichloroethane are split. The conversion is 55%.

The hot gas leaving the reaction furnace at a temperature of 540° C. is routed through a single-tube heat exchanger with a U-tube flanged to one end. Deionized water is used as coolant. The residence time of the reaction gas in the heat exchanger is 4 seconds. The temperature measured at the outlet of the U-tube is 200° C. The average cooling rate of the reaction gas is 85° C./s at a pressure drop of the reaction gas in the heat exchanger of 0.2 MPa.

The indirect heat exchange with the hot reaction gas permits an hourly production of 1.65 parts by weight of steam at a pressure of 0.8 MPa. It is fed into the steam system of the column for separating the vinyl chloride and serves for heating reboilers. The service time of the heat exchanger is 4 months. During this time, the U-tube is subject to the formation of coke deposits of 0.3 cm thickness. At this time, the heat exchanger requires cleaning. The gas stream cooled to 200° C. by the indirect heat exchange is not sent into a vessel where 1200 parts by weight of 1,2-dichloroethane at 40° C. recovered from the reaction products are injected for each portion of 100 parts by weight by reaction feed gas. The reaction products undergo cooling to 70° C. and partial condensation. By scrubbing the dichloroethane, small carbon black particles are retained from the gas stream and separated from the liquid dichloroethane phase by filtration.

The splitting of the reaction gas is then realized by known methods by separating hydrogen chloride and vinyl chloride from unconverted 1,2-dichloroethane and recovery of the latter substance.

The coolant absorbs heat at a rate of 390 kJ/h per kg of reaction gas; this energy is utilized for heating process equipment for the splitting of the reaction products and for the reuse of recovered 1,2-dichloroethane.

EXAMPLE 2

Reference is made to the flowsheet FIG. 2.

A reaction furnace is fed hourly with 9.98 parts by weight of 1,2-dichloroethane having the same composition as defined for example 1, the final reaction temperature and the conversion rate corresponding to example 1. The cooling of the reaction gas is performed in three stages. In the first stage, the reaction gas is cooled from an inlet temperature of 540° C. to an outlet temperature of 400° C. by injecting 2.33 parts by weight per hour of liquid unconverted 1,2-dichloroethane of 40° C. The injected 1,2-dichloroethane undergoes vaporization and a small portion is split into vinyl chloride and hydrogen chloride. In the second stage, the reaction gas is sent into a single-tube heat exchanger. Mineral oil Marlotherm is used as coolant and is subjected to recycling. The residence time of the reaction gas in the heat exchanger is 3.3 seconds. A temperature of 190° C. is measured at the outlet of the heat exchanger tube. The average cooling rate of the reaction gas is 63° C./s. By the indirect heat exchange with the hot reaction gas, the temperature of the mineral oil rises to 180° C., the heat absorption being 280 kJ/h per kg of reaction gas. This energy is utilized for heating process equipment for splitting the reaction products and for the reuse of recovered 1,2-dichloroethane.

In a third stage, the product leaving the heat exchanger is cooled to 70° C. as described in example 1 by injecting 1,2-dichloroethane at 40° C. before being subjected to further processing. After 6 months, the coke deposits in the inner tube of heat exchanger 2 have attained a thickness of about 3 mm. The heat exchanger is then cleaned for improving its efficiency.

EXAMPLE 3

Reference is made to the flowsheet FIG. 1.

The reaction furnace is fed hourly with 45.33 parts by weight of 1,2-dichloroethane having the same composition as defined for example 1. The conversion is 50%, the reaction furnace outlet temperature is 500° C. The cooling of the reaction gas is performed in two stages. In the first stage the temperature is lowered by 370° C.

from 500° C. to 130° C. by indirect cooling with the demineralized water in the single-tube heat exchanger, the hourly steam production being 10.6 parts by weight of stream at a pressure of 0.25 MPa. At the system pressure of 1.7 MPa, partial condensation of unconverted 1,2-dichloroethane from the cracking process takes place at a temperature of 130° C. At a residence time of the reaction gas of 6.2 seconds and an average cooling rate of 60° C./s, the service time of the heat exchanger is approximately two months.

After leaving the heat exchanger, the product is cooled from 130° C. to 60° C. by the injection of cold 1,2-dichloroethane as described for example 1, before being subjected to further processing.

EXAMPLE 4

Reference is made to the flowsheet FIG. 2.

The reaction furnace is fed hourly with 45.33 parts by weight of 1,2-dichloroethane having the same composition as defined for example 1, the final reaction temperature and the conversion corresponding to example 3. The cooling of the reaction gas is performed in three stages as described for example 2.

In the first stage, the reaction gas is cooled to 370° C. by injecting 10.46 parts by weight per hour of unconverted liquid 1,2-dichloroethane at 40° C. from the cracking process.

In the second stage, the temperature is lowered to 130° C. by indirect heat exchange, the steam production being 10 parts by weight per hour. At a residence time of 6 seconds of the reaction gas in the heat exchanger and an average cooling rate of 40° C./s the service time of the heat exchanger is approximately 4 months. A standby heat exchanger is put in operation to avoid a shutdown of the cracking process while the service heat exchanger is being cleaned.

After leaving the heat exchanger, the product is cooled from 130° C. to 60° C. by injecting cold 1,2-dichloroethane as described for example 1, before being subjected to further processing.

COMPARATIVE TEST A

Reference is made to the flowsheet FIG. 1.

The test was performed as described for the process according to example 1, except that the average cooling rate of the hot reaction gas from 540° to 200° C. was only 20° C./s. After a few days of operation, the pressure drop across the heat exchanger had risen from 0.2 to 0.5 MPa. After 2 weeks of operation, the thickness of coke deposits in the heat exchanger tube was 5 mm.

COMPARATIVE TEST B

Reference is made to the flowsheet FIG. 2.

The test was performed as described for the process according to example 4, except that the average cooling rate of the hot reaction gas from 370° C. to 130° C. was only 15° C./s. The phenomena were very similar to those outlined for comparative test A. The heat exchanger was subject to rapid formation of coke deposits. The service time of the heat exchanger was less than 4 weeks.

EXAMPLE 5.

Reference is made to the flowsheet FIG. 3.

The reaction furnace is fed hourly with 9.98 parts by weight of 1,2-dichloroethane having the same composition as defined for example 1. At a pressure of 2.1 MPa, the cracking rate per hour is 5.46 parts by weight of 1,2-dichloroethane. The conversion is 55%.

The hot gas leaving reaction furnace 1 at a temperature of 540° C. is sent through a single-tube heat exchanger 2 with a U-tube flanged to one end. Dionized water 3 is used as coolant. The residence time of the reaction gas in the heat exchanger is 4 seconds. A temperature of 220° C. is measured at the outlet of the U-tube. The average cooling rate of the reaction gas is 85° C./s at a pressure drop of 0.2 MPa of the reaction gas in the heat exchanger.

The indirect heat exchange with the hot reaction gas permits an hourly production of 1.4 parts by weight of steam 4 at a pressure of 0.8 MPa. It is fed into the steam system of the column for separating the vinyl chloride and serves for heating reboilers. The service time of the heat exchanger is 6 months.

The temperature of the gas stream lowered to 220° C. by indirect heat exchange is further reduced to 140° C. in a second heat exchanger 24 of the same U-type but with a cross-sectional area of the tube reduced by 40%. The average cooling rate is 85° C./s at a pressure drop of 0.1 MPa of the reaction gas in the heat exchanger. The stream production is 0.6 ton/hour at a pressure of 0.2 MPa. The energy recovered is primarily utilized for the distillation of 1,2-dichloroethane.

For withdrawing the carbon black from the second heat exchanger a liquid substantially consisting of 1,2-dichloroethane from device 6 is admixed to the reaction gas ahead of the inlet to the second heat exchanger, admixing being performed intermittently every 100 hours for a time of 5 minutes and at a rate of 2.7 kg/min. per kg/min. of reaction gas. The temperature of the admixed liquid is 60° C.

The heat exchanger has a service time up to 6 months. During this time, coke deposits in the U-tube attain a thickness of about 4 mm.

For further reducing the temperature and for splitting the gas stream, the process continues as described for example 1:

The gas stream cooled to 140° C. is sent to a vessel where 70 parts by weight of 1,2-dichloroethane at 40° C. recovered from the reaction products is injected for every 10 parts by weight of reaction gas admitted. The gas stream undergoes cooling to 50° C. and further condensation of the reaction products. By the scrubbing with dichloroethane, small carbon black particles are separated from the gas stream and retained by filtration from the liquid dichloroethane phase in device 27. The splitting of the reaction gas is then performed along known methods by separating hydrogen chloride from the vinyl chloride and the unconverted dichloroethane in the so-called HCl column 13. The column received three product streams, viz. a liquid stream through line 8 substantially consisting of 1,2-dichloroethane, another liquid stream through line 11 substantially consisting of vinyl chloride and a gaseous stream through line 12 substantially consisting of hydrogen chloride. For splitting the gas phase from vessel 6 into another liquid and gas phase, the gas stream is cooled to about 20° C. by indirect heat exchange in device 10.

We claim:

1. A process for the manufacture of vinyl chloride in a reaction furnace by thermal cracking of 1,2-dichloroethane, wherein reaction gas leaving the reaction furnace is cooled in two stages, in one of which stages the gas is cooled indirectly by a liquid or gaseous coolant for subsequent splitting by distillation, said process incorporating the improvement which comprises cooling the reaction gas mixture to a temperature within the range of 220° to 120° C. in the indirect stage at an average cooling rate, in degrees C. per second, of at least 1/10 of the temperature in degrees C. of the gas mixture entering the indirect stage, and the reaction gas mixture together with any condensate resulting from this mixture being further cooled directly or indirectly in at least one downstream stage.

2. A process according to claim 1, incorporating the improvement which comprises the reaction gas mixture leaving the reaction furnace at a temperature of 560° to 480° C. and being cooled directly in a first stage by contacting it with a liquid product containing at least 50% by weight of 1,2-dichloroethane and being subsequently cooled indirectly with a liquid or gaseous coolant, the indirect cooling being initiated only when the reaction gas mixture has reached a temperature level of about 430° to 350° C. and being continued to a temperature level of 220° to 120° C., the heat transferred to the coolant being utilized for heating any process equipment and the reaction gas mixture together with any condensate resulting from this mixture being further cooled directly or indirectly in at least one downstream stage.

3. A process according to claim 2, incorporating the improvement which comprises cooling the reaction gas mixture to a temperature level of 220° to 120° C. at an average cooling rate, per second, of ¼ to 1/9 of the temperature in terms of °C. at which this mixture enters the indirect cooling stage.

4. A process according to claim 3, incorporating the improvement which comprises initiating the indirect cooling at a temperature of 400° to 370° C.

5. A process according to claim 1, incorporating the improvement which comprises cooling the reaction gas mixture in a first stage by indirect cooling from the reaction furnace outlet temperature to about 220° C., lowering its temperature to about 140° C. by partly direct, partly indirect cooling in a second stage while a liquid substantially consisting of 1,2-dichloroethane is added intermittently, and subsequently cooling it directly or indirectly in at least one further stage to the inlet temperature of the column in which the hydrogen chloride is separated from the products of thermal cracking of 1,2-dichloroethane.

6. A process according to claim 5, incorporating the improvement which comprises admitting the liquid substantially consisting of 1,2-dichloroethane to the second cooling stage at intervals of 20 to about 500 hours for a period of 1 to about 30 minutes and at a rate of 1.5 to 5.0 kg/min. per kg/min. of reaction gas.

7. A process according to claim 6, incorporating the improvement which comprises the liquid substantially consisting of 1,2-dichloroethane having a temperature of 20° to 70° C. before being admitted to the second cooling stage.

8. A process according to claim 7, incorporating the improvement which comprises using in the first stage for indirect cooling a coolant which is liquid at 100° C. and whose vapour pressure does not exceed 2.5 MPa at 220° C.

9. A process according to claim 8, incorporating the improvement which comprises using for indirect cooling in the first stage a coolant whose boiling point is situated between 70° to 110° C. at a pressure of 98.1 kPa.

10. A process according to claim 9, incorporating the improvement which comprises the coolant being 1,2-dichloroethane.

* * * * *

UNITED STATES PATENT AND TRADEMARK OFFICE
CERTIFICATE OF CORRECTION

PATENT NO. : 4,324,932
DATED : April 13, 1982
INVENTOR(S) : Gerhard Link, Josef Riedl, Walter Frohlich and Reinhard Krumbock It is certified that error appears in the above-identified patent and that said Letters Patent are hereby corrected as shown below:

On the title page, please list the assignee as follows:

UHDE GmbH
Dortmund Germany

Signed and Sealed this

Tenth Day of July 1984

[SEAL]

*Attest:*

*Attesting Officer*

GERALD J. MOSSINGHOFF
*Commissioner of Patents and Trademarks*